United States Patent [19]

Ferlazzo et al.

[11] 4,014,925
[45] Mar. 29, 1977

[54] PROCESS FOR PREPARING METHYL ACRYLATE OR MIXTURES OF METHYL ACRYLATE AND ACRYLIC ACID

[75] Inventors: Natale Ferlazzo, Segrate (Milan); Gian Fausto Buzzi, Arona (Novara); Marcello Ghirga, Bresso (Milan); Benedetto Calcagno, Milan, all of Italy

[73] Assignee: Societa' Italiana Resine S.I.R. S.p.A., Milan, Italy

[22] Filed: Nov. 5, 1974

[21] Appl. No.: 521,016

[30] Foreign Application Priority Data

Nov. 28, 1973 Italy ............................. 31746/73

[52] U.S. Cl. .................... 260/486 R; 252/437; 252/459; 260/530 N
[51] Int. Cl.² ........................................ C07C 69/54
[58] Field of Search .............................. 260/486 R

[56] References Cited
UNITED STATES PATENTS

| | | | |
|---|---|---|---|
| 3,253,025 | 5/1966 | Brill | 260/486 R |
| 3,539,620 | 11/1970 | Coyne et al. | 260/486 R |
| 3,819,685 | 6/1974 | Grasselli et al. | 260/486 R |

Primary Examiner—Paul J. Killos
Attorney, Agent, or Firm—Sughrue, Rothwell, Mion, Zinn & Macpeak

[57] ABSTRACT

Methyl acrylate or a mixture of methyl acrylate with acrylic acid are prepared by passing through a fluidized bed of catalyst a gaseous mixture comprising acrolein, methanol and oxygen fed at the bottom of the catalytic bed. A further amount of methanol is fed at one intermediate point at least, between the top and bottom of the catalytic bed. The catalyst is defined by one of the general formulae:

$Mo_a V_b Me_c O_x$
$Mo_a W_d Me_c O_y$
$Mo_a V_b W_d Me_c O_z$ wherein Me is Cr, Mn, Fe, Co, Ni, Cu, Zn, Ag, Cd, Au, Hg, Na, Ba, Ca, Ce, Bi, Th, U, Pb, Sb, Sn, P or B; and wherein $a$ is a value from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5.

16 Claims, No Drawings

PROCESS FOR PREPARING METHYL ACRYLATE OR MIXTURES OF METHYL ACRYLATE AND ACRYLIC ACID

BACKGROUND OF THE INVENTION

1. Field of the Invention

The invention relates to an improved process for preparing methyl acrylate or mixtures of the latter with acrylic acid.

2. Description of the Prior Art

The methyl ester of acrylic acid is a valuable product which is employed more particularly in preparing polymeric products of wide use. Acrylic acid is employed to a great extent in actual practice, too.

Various processes are known in the art for preparing the esters of acrylic acid, such as those based on hydrolysis of acrylonitrile or on the reaction of acetylene, carbon monoxide and an alcohol in the presence of a nickel carbonyl complex.

According to a widely used industrial process, propylene is oxidized to acrolein on suitable oxidation catalysts and the resulting acrolein is catalytically oxidized to acrylic acid.

Finally, the acid is esterified by reaction with a lower aliphatic alcohol in a further reaction step.

The above described process is rather complex owing to the multiple reaction steps which necessitate a number of onerous purifications and recyclings. Moreover, the overall yield of acrylic ester is relatively low.

According to a further process known in the art, propylene is directly oxidized to acrylic acid on suitable catalysts in one reaction step. With this process the conversion of propylene to acrylic acid is generally very low and large quantities of unsaturated aldehyde mixed with the unsaturated carboxylic acid are moreover produced.

It is therefore necessary to separate the unsaturated aldehyde and unaltered propylene from the reaction products, as well as to purify and recycle such products with the inherent disadvantages.

According to our prior U.S. patent application Ser. No. 469,446 filed May 13, 1974, now abandoned, the methyl ester of the acrylic acid is prepared by contacting a gaseous flow comprising acrolein, oxygen and methanol with special catalysts. This is a considerable simplification in the process for preparing methyl acrylate.

Moreover, according to the cited application, acrylic acid can be produced together with methyl acrylate.

The process is so flexible that adjustment of the ratio of acrylic acid to its corresponding methyl ester in the reaction products is made possible simply by varying the acrolein/methanol ratio in the gaseous feed to the catalyst.

Suitable catalysts for such conversion are oxides of molybdenum, vanadium and/or tungsten, possibly combined with further metal oxides.

SUMMARY OF THE INVENTION

The present invention affords considerable improvements in the preparation of methyl acrylate or mixtures thereof with acrylic acid in the process (oxyesterification process) in which a gaseous mixture containing acrolein, methanol and oxygen is contacted with the above described catalysts (oxyesterification catalysts). The improvements mainly reside in an improved reaction selectivity which may reach up to about 97–100% in useful products and accordingly in almost full suppression of combustion processes and further secondary reactions.

According to the process of the invention a reacting gaseous flow containing acrolein and oxygen is delivered at the bottom of a bed of fluidized catalyst particles, methanol being continuously delivered in part at the bottom of the catalytic bed as a gaseous mixture with the reacting gaseous flow and the remaining portion at least at one intermediate point between the top and bottom of the catalytic bed, the catalyst being defined by one of the following general formulae:

1. $Mo_a V_b Me_c O_x$
2. $Mo_a W_d Me_c O_y$
3. $Mo_a V_b W_d Me_c O_z$ wherein Me stands for: chromium, manganese, iron, cobalt, nickel, copper, zinc, silver, cadmium, gold, mercury, sodium, barium, calcium, cerium, bismuth, thorium, uranium, lead, antimony, tin, phosphorus or boron; $a$ can range from 6 to 12; $b$ can range from 1 to 6; $c$ can range from 0 to 5; $d$ can range from 1 to 6; $x$ can range from 20.5 to 58.5; $y$ can range from 21 to 61.5 and $z$ can range from 23.5 to 76.5.

DETAILED DESCRIPTION OF THE INVENTION

The catalyst can be prepared by a process comprising the steps of dissolving in water compounds of the metals present in the catalyst, precipitating the compounds by evaporation of the solution and heat-treating at high temperature the thus separated solids.

Moreover, a support for the catalyst is conveniently employed in order to impart to the catalyst higher mechanical properties such as is required in fluidization. Silica is more particularly convenient for the purpose and can be present in the supported catalyst in a proportion of 10 to 80% by weight.

In preparing the supported catalyst, ammoniacal soluble silica (ammonium silicate solution) can be added to the solution of the compounds, the resulting solution being treated as described above or spray dried.

It is also possible to impregnate silica particles with the solution of the compounds, then effect heat treatment of the impregnated support at high temperature.

The catalyst is preferably employed in the form of granules or microspheroidal particles of a size of 15 to 150 microns.

The gaseous flow delivered at the bottom of the catalytic bed typically contains from 1 to 8% by volume acrolein and from 0.5 to 10% by volume oxygen, the remainder consisting substantially of inert gases. It is moreover convenient to maintain the acrolein: oxygen molar ratio from 0.1:1 to 4:1, preferably from 0.2:1 to 2:1.

The catalyst is conveniently fed with methanol in a total proportion of from 0.2 to 5 moles, preferably 0.5 to 1.3 moles, per 1 mole of acrolein.

The fundamental aspect of the process of the invention resides in delivering the said methanol in part only together with the gaseous flow at the bottom of the catalytic bed, the remaining portion being delivered laterally at one or a number of intermediate points along the height of the fluidized catalytic bed.

The number of these delivery points along the catalytic bed can be as high as, say, five, although three inlets should preferably not be exceeded in actual practice.

The best results are obtained by delivering increasing quantities of methanol to the catalytic bed starting from the bottom towards the top.

At any rate, the methanol is conveniently delivered at the bottom of the catalytic bed in a proportion, with respect to its total, not exceeding 30, preferably not exceeding 20%. The methanol can be in a pure form or diluted with other gases such as air, nitrogen and steam.

In a preferred embodiment of the process of the invention the fluidized catalytic bed is formed in a reactor comprising a number of perforated trays or other perforated members arranged horizontally within the reactor. In this case it may be useful to supply a methanol flow at each region defined by two contiguous trays or members.

The above-described gaseous mixture supplied to the catalyst usually contains, in addition to acrolein, oxygen and methanol, also inert gases such as, for example, nitrogen, carbon dioxide and steam.

The temperature usually is from 180° to 320° C (220° to 280° C being the preferred range) and the contact period is from 0.1 to 40 seconds (1–20 seconds being the preferred range).

The process can be carried out at atmospheric pressure or at a very slightly increased pressure such as up to 5 kg/sq.cm.

Under these conditions the selectivity for the useful reaction products (methyl acrylate, acrylic acid) always exceeds 90% on a molar basis with respect to the moles of converted acrolein. The conversion of acrolein generally exceeds 95% with respect to the feed.

According to an embodiment of the process of the invention, the above-described gaseous flow comprises the gases obtained in the catalytic oxidation of propylene to acrolein, possibly admixed with oxygen and/or an inert gas. The process then comprises a first step (oxidation step) at which propylene is essentially converted to acrolein, and a further step (oxyesterification step) of converting acrolein to methyl acrylate and possibly also to acrylic acid in the above described manner.

Catalysts useful for oxidation of propylene are those known in the art such as, for example, couprous oxide, mixed oxides of bismuth and molybdenum or cobalt and antimony oxide in combination with further metal oxides. Further useful catalysts are combinations of oxides comprising tungsten oxide, or silver selenite activated with cuprous oxide or cobalt molybdate in combination with tellurium oxide. The catalysts can be employed in the form of a stationary, fluidized or movable bed although, preferably, a fluidized bed technique is employed. At any rate, the catalyst is supplied with a gaseous flow containing 1 to 8% by volume propylene and 4 to 20% by volume oxygen, the remaining percentage being inert gases such as nitrogen, carbon dioxide or steam.

More particularly, the molar ratio of propylene to oxygen is maintained in the gaseous flow at from 0.2:1 to 1:2 (the preferred range being from 0.3:1 to 0.6:1). The temperature is from 300° to 400° C (the preferred range being from 330° to 370° C), the contact period under the reaction conditions being from 1 to 20 seconds (the preferred range being from 2 to 6 seconds). Finally, it is possible to operate at atmospheric pressure or to adopt only a slightly increased pressure such as up to 3 kg/sq.cm.

By operating under the above conditions the propylene conversion normally amounts to 95 to 98% with respect to the feed, the selectivity for acrolein amounting to 85 to 90% with respect to the reacted propylene.

The gaseous flow discharged from the first step is then enriched with methanol and possibly with oxygen and/or an inert gas to obtain the previously defined gaseous mixture suitable for the next oxyesterification step.

Finally, methyl acrylate, and acrylic acid if present, is removed by any known method from the gaseous effluent issuing from the oxyesterification zone. Thus, for example, the gases can be absorbed by bubbling and extraction in water, followed by a distillation step. A fractionated condensation and subsequent absorption in water can alternatively be effected.

The following experimental examples further illustrate the invention.

EXAMPLE 1

60 liters of water are charged into an enamelled 200 liter boiler heated by a steam jacket. The temperature is raised to 90° C and 2,430 g of ammonium paramolybdate $((NH_4)_6Mo_7O_{24}\cdot 4H_2O)$ and subsequently 602.5 g ammonium metavanadate $(NH_4VO_3)$ are dissolved while stirring.

354 g. of tungstic acid $(H_2WO_4)$ are separately dissolved in an ammoniacal aqueous solution formed of 5 liters of water and 1 liter of 28% by weight aqueous ammonia.

The latter solution is poured into the former and the whole is concentrated over a period of 6 hours at 90° C to a residual volume of 30 liters. The concentrated solution is allowed to cool and admixed with a solution of 1,728 g of copper nitrate $(Cu(NO_3)_2\cdot 3H_2O)$ in 7 liters of water.

The resulting solution is admixed with 2.5 liters of 28% by weight aqueous ammonia and stirring is continued for a few minutes, whereupon 4.2 liters of silica hydrosol (a commercial product known under the trade name LUDOX AS containing 30% by weight silica) diluted with 4 liters of water are admixed.

The resulting solution is stirred for a few minutes then centrifugally sprayed co-currently with air heated at 400° C. The result is a microspheroidal solid product of 20 to 100 microns in grain size, which is heated for 2 hours at 300° C in an air stream and for 2 hours at 390° C in a bed fluidized with nitrogen.

The resulting catalyst has a surface area of 23 sq.m/g and bulk density of 1.1 g/ml.

EXAMPLE 2

Two reactors of stainless steel AISI 316, of a vertically elongated tubular form of 60 mm in bore diameter, are employed in series.

The first reactor is charged with 1.5 liters of a known catalyst for oxidizing propylene to acrolein, formed of bismuth phosphomolybdate particles of a grain size of about 30 to 80 microns.

The second reactor is charged with 1.5 liters catalyst prepared as described in Example 1. The first reactor is operated with the catalyst in the form of a fluidized bed, and is fed at the bottom at a rate of 584 liters/hr (measured at 20° C and ambient pressure) with a gaseous mixture containing 4.0% by volume propylene, 10.5% by volume oxygen, 4.0% by volume steam, the remaining percentage being nitrogen.

The first reactor is further operated at a temperature of 350° C with a contact period of 4 seconds measured under reaction conditions, the propylene conversion amounting to 95% and the selectivity for acrolein and acrylic acid amounting to 90% with respect to the reacted propylene.

The gaseous flow issuing at the top of the first reactor has the following composition by volume: propylene 0.2%, acrolein 3.2%, CO and $CO_2$ 1.2%, acrylic acid 0.4%, oxygen 4.8%, steam 8.3%, the remaining percentage being nitrogen.

This gaseous flow is admixed with methanol in a proportion of 0.2% by volume, the resulting mixture being delivered at the bottom of the second reactor. The second reactor is operated with a fluidized catalytic bed at a temperature of 256° C with a contact period of 4.7 seconds.

At ⅓ and ⅔ of the height of the fluidized catalytic bed, measured from the bed bottom, gaseous methanol is delivered in a proportion of 0.4 and 0.6% by volume, respectively, with respect to the total volume of the gaseous mixture delivered at the reactor bottom.

The gases issuing at the top of the second reactor are subjected to gas-chromatographic analysis. The determined acrolein conversion amounts to 98.3%, with the selectivity for methyl acrylate and acrylic acid amounting to 97.8% with respect to the converted acrolein. Moreover, the methyl acrylate yield with respect to the methanol feed amounts to 80.5%.

EXAMPLE 3

A support for the catalyst is employed, which consists of a microspheroidal commercial silica having following properties:
Surface area: about 600 sq.m/g
pore volume: about 1.1 ml/g
bulk density: about 0.45 g/ml
SiO content: above 99.5%
$Al_2O_3$ content: below 0.3%
$Na_2O$ content: below 0.03%
Fe content: below 0.03%.

Moreover, 80 to 90% of the silica particles are of a grain size of 30 to 100 microns.

2,370 g of the above described silica are impregnated with an aqueous solution containing 315 g of copper nitrate $(Cu(NO_3)_2 \cdot 3H_2O)$ dissolved in 2,100 ml water, at room temperature, then dried in an oven for 2 hours at 120° C.

An aqueous solution of the molybdenum, vanadium and tungsten salts is prepared in the manner described in Example 1 from 810 g of ammonium paramolybdate, 210 g of ammonium metavanadate and 118 g of tungstic acid in 10 liters water.

The support previously treated with the copper nitrate solution is impregnated at 80° C with the resulting solution concentrated to a volume of 2.1 liters, then dried for 2 hours at 120° C and treated for 2 hours at 300° C in an air stream and for 2 hours at 400° C in a nitrogen stream. The resulting catalyst has a bulk density of 0.63 g/ml.

EXAMPLE 4

This example comprises two consecutive steps, the first of which is oxidation of propylene to acrolein exactly as described in Example 2. A gaseous flow is obtained at the top of the first reactor, consisting of 0.2% propylene, 3.2% acrolein, 0.4% acrylic acid, 4.8% oxygen, 8.3% steam, 1.2% CO and $CO_2$, the remaining percentage being nitrogen.

This gaseous flow is admixed with methanol in a proportion of 0.2% by volume and steam in a proportion of 8% by volume.

The resulting gaseous mixture is delivered at the bottom of a vertical tubular reactor of stainless steel AISI 316, 60 mm in bore diameter, containing 2 liters of the catalyst prepared as described in Example 3.

The second step is operated with the fluidized catalyst at a temperature of 230° C with a constant period of 4.3 seconds.

At ⅓ and ⅔ of the height of the catalytic bed measured from the bed bottom, gaseous methanol is delivered in a proportion of 0.2 and 0.4%, respectively, by volume, with respect to the volume of the gaseous mixture delivered to the reactor bottom.

The reaction gases discharged at the top of the second reactor are subjected to gas chromatograhic analysis. The determined acrolein conversion amounts to 97%, with the selectivity for methyl acrylate and acrylic acid with respect to converted acrolein amounting to 96.7%.

The methyl acrylate yield with respect to the methanol feed amounts to 87%.

We claim:

1. A method for preparing methyl acrylate or a mixture of methyl acrylate and acrylic acid by contacting acrolein, methnol and oxygen with a catalyst, which comprises continuously delivering said methanol in part at the bottom of a bed of the fluidized catalyst as a gaseous mixture with a gaseous flow comprising said acrolein and oxygen and in part at at least one intermediate point between the top and bottom of the fluidized catalyst bed, said catalyst being selected from the group consisting of compounds defined by the following formulae:

$$Mo_aV_bMe_cO_x$$
$$Mo_aW_dMe_cO_y$$
$$Mo_aV_bW_dMe_cO_z$$

wherein Me is an element selected from the group consisting of chromium, manganese, iron, cobalt, nickel, copper, zinc, silver, cadmium, gold, mercury, sodium, barium, calcium, cerium, bismuth, thorium, uranium, lead, antimony, tin, phosphorus and boron; and wherein $a, b, c, d, x, y, z$ are respectively: $a$ from 6 to 12, $b$ from 1 to 6, $c$ from 0 to 5, $d$ from 1 to 6, $x$ from 20.5 to 58.5, $y$ from 21 to 61.5 and $z$ from 23.5 to 76.5.

2. The method of claim 1, wherein the catalyst is supported on silica present in a proportion from 10 to 80% by weight in the supported catalyst.

3. The method of claim 1, wherein said gaseous flow comprises from 1 to 8 vol % acrolein and from 0.5 to 10 vol. % oxygen, with the molar ratio of acrolein to oxygen being from 0.1:1 to 4:1.

4. The method of claim 1, wherein the methanol is fed in a total proportion of from 0.2 to 5 moles for each mole of acrolein.

5. The method of claim 1, wherein the methanol is fed at the bottom of the catalyst bed in a proportion not exceeding 30% by weight of the total quantity of methanol.

6. The method of claim 1, wherein the methanol is fed at the bottom of the catalyst bed in a proportion not exceeding 20% by weight of the total quantity of methanol.

7. The method of claim 1, wherein said intermediate points are not more than five.

8. The method of claim 1, wherein said intermediate points are not more than three.

9. The method of claim 1, wherein the temperature is from 180° to 320° C and the contact period is from 0.1 to 40 seconds.

10. The method of claim 1, wherein the temperature is from 220° to 280° C and the contact period is from 1 to 20 seconds.

11. The method of claim 1, wherein said gaseous flow comprises the gases obtained in the catalytic oxidation of propylene to acrolein.

12. The method of claim 1, wherein said gaseous flow consists essentially of the gases obtained in the catalyst oxidation of propylene to acrolein and admixed with oxygen.

13. The method of claim 3, wherein the methanol is fed in a total proportion of from 0.2 to 5 moles for each mole of acrolein, with the proportion of methanol fed at the bottom of the catalyst bed not exceeding 20% by weight of the total quantity of methanol and the remainder of the methanol being fed at not more than five intermediate points, and with the temperature being from 180° to 320° C and the contact period being from 0.1 to 40 seconds.

14. The method of claim 13, wherein said gaseous flow comprises the gases obtained in the catalytic oxidation of propylene to acrolein.

15. The method of claim 1, wherein said gaseous flow consists essentially of the gases obtained in the catalytic oxidation of propylene to acrolein and admixed with at least one inert gas.

16. The method of claim 1, wherein said gaseous flow consists essentially of the gases obtained in the catalytic oxidation of propylene to acrolein and admixed with oxygen and at least one inert gas.

* * * * *